United States Patent [19]

Yamada

[11] Patent Number: 5,688,285
[45] Date of Patent: Nov. 18, 1997

[54] GRAFT BONE FIXATION TOOL

[76] Inventor: Ikufumi Yamada, Kumagaikata, 2-1-16, Ogawa, Machida-city, Tokyo, Japan

[21] Appl. No.: 576,867

[22] Filed: Dec. 21, 1995

Related U.S. Application Data

[63] Continuation-in-part of Ser. No. 520,371, Aug. 29, 1995.

[51] Int. Cl.$^6$ .................................................. A61F 2/08
[52] U.S. Cl. .................................................. 606/104; 606/73
[58] Field of Search .................................. 606/73, 72, 104, 606/77; 81/436, 437, 439

[56] References Cited

U.S. PATENT DOCUMENTS

| | | | |
|---|---|---|---|
| 2,248,054 | 7/1941 | Becker | 606/104 |
| 4,759,352 | 7/1988 | Lozier | 128/92 |
| 4,858,601 | 8/1989 | Glisson | 606/73 |
| 4,927,421 | 5/1990 | Goble et al. | |
| 5,172,790 | 10/1992 | Rosenberg et al. | 606/73 |
| 5,341,705 | 8/1994 | Lin | 81/439 |
| 5,354,299 | 10/1994 | Coleman | 606/73 |
| 5,403,136 | 4/1995 | Mathys | 606/73 |
| 5,423,819 | 6/1995 | Small et al. | 606/73 |
| 5,458,064 | 10/1995 | Schmieding | 606/104 |
| 5,571,139 | 11/1996 | Jenkins, Jr. | 606/73 |

FOREIGN PATENT DOCUMENTS

| | | |
|---|---|---|
| 0 172 130 | 2/1986 | European Pat. Off. . |
| 0 674 880 | 10/1995 | European Pat. Off. . |
| 0 682 917 | 11/1995 | European Pat. Off. . |
| 2 717 070 | 9/1995 | France . |
| 827050 | 5/1981 | U.S.S.R. ................... 606/73 |

*Primary Examiner*—Michael Buiz
*Assistant Examiner*—Julian W. Woo
*Attorney, Agent, or Firm*—Skjerven, Morrill, MacPherson, Franklin & Friel LLP

[57] ABSTRACT

Disclosed is an improved screw member adapted to be threaded into a gap between two bone parts in BTB tendon transfer surgical operations, and a fixation tool for engaging the screw member. The screw member typically consists of a hollow cylindrical member comprising an axial bore having a hexagonal cross section, and an outer circumferential surface provided with a strictly straight thread. The fixation tool comprises a transmission shaft having an intermediate section having a hexagonal cross section complementary to that of the axial bore of the screw member. Because the transmission shaft is entirely passed through the axial bore of the screw member, the torque for turning the screw member can be positively transmitted to the screw member, and the transmission shaft provides a positive guide action for the insertion of the screw member. The transmission shaft may be either axially slidably but rotatively integrally engaged to a handle grip or integrally attached to a handle grip.

5 Claims, 10 Drawing Sheets

GRAFT BONE FIXATION TOOL

CROSS-REFERENCE TO RELATED APPLICATION

This application is a continuation-in-part of U.S. patent application Ser. No. 08/520,371 entitled "Taper-less Screw and Screwdriver" filed on Aug. 29, 1995.

TECHNICAL FIELD

The present invention relates to a graff bone fixation tool for securing a graft bone piece in a bore formed in a bone, and in particular to a graff bone fixation tool for use in tendon transfer surgical operations in the field of orthopedic surgery.

BACKGROUND OF THE INVENTION

Figure 1A:
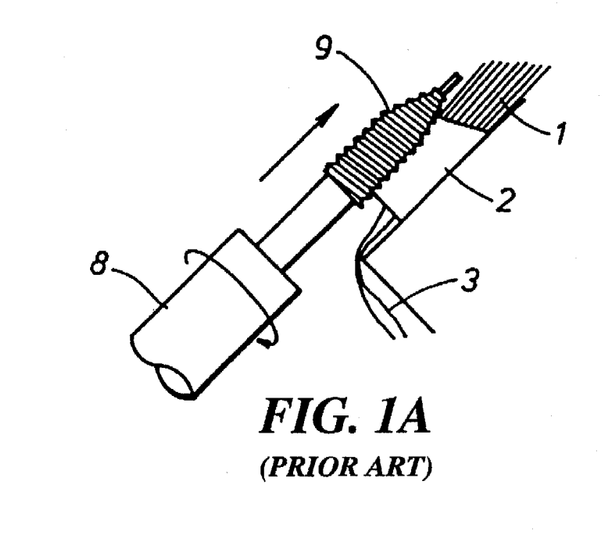
FIGS. 1a to 1c are schematic views showing the tendon transfer surgery using the conventional graft bone fixation tool.
Figure 1B:
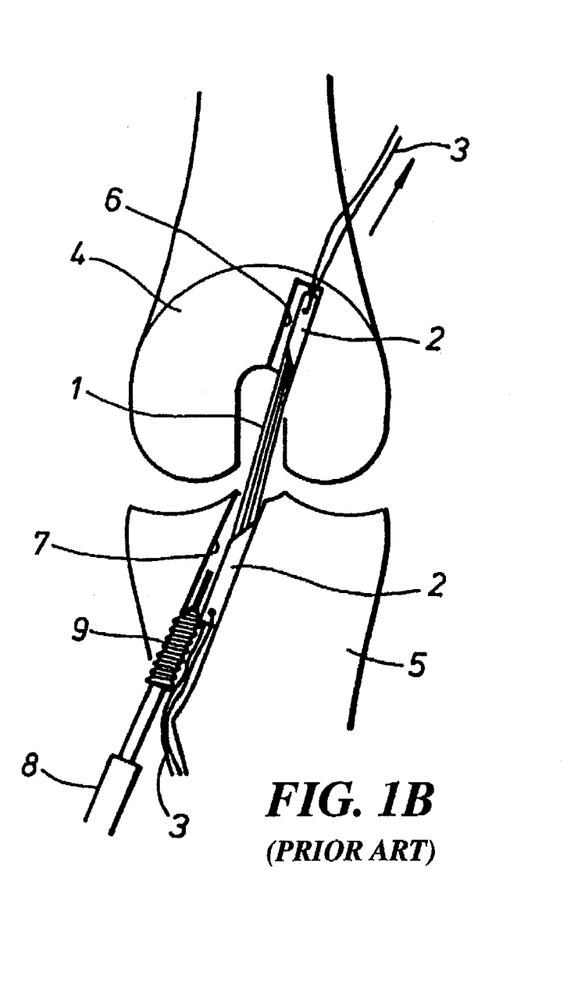
Figure 1C:
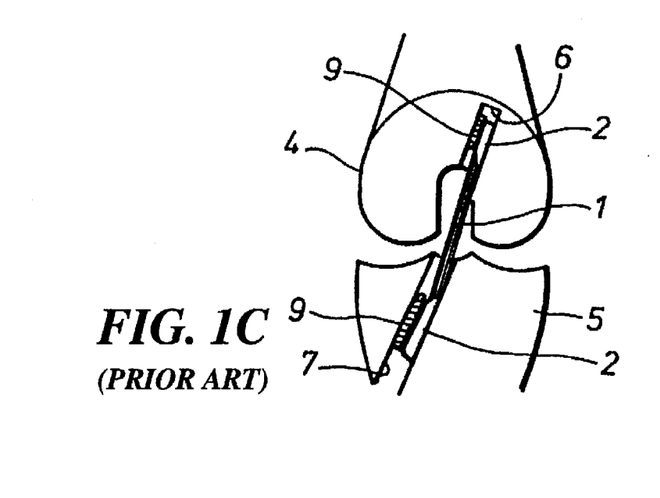

In the field of orthopedic surgery, the method known as the BTB (bone-tendon-bone) method has been used for reconstructing a severed tendon as illustrated in FIGS. 1a to 1c. According to the BTB method, a graft consisting of two pieces of bone 2 joined by a tendon 1 is harvested typically from a patella and an adjacent tibia, and sutures 3 are passed through openings formed in the bone pieces 2. Meanwhile, bore 6 and 7 are drilled in the femur 4 and the tibia 5 at a joint whose tendon is severed or otherwise damaged, and is therefore desired to be reconstructed.

By using the sutures 3, the graft tendon 1 along with the graff bone pieces 2 are passed through the bores 6 and 7 formed in the femur 4 and the tibia 5 so that the graft tendon 1 extends between the femur 4 and the tibia 5. A screw member 9 is then threaded into a gap defined between the inner wall of the bore 7 of the tibia 5 and the corresponding bone piece 2 by using a fixation tool 8 so that the bone piece 2 may be securely pressed against the inner wall of the bore 7 of the tibia 5. Similarly, another screw member 9 is threaded into a gap defined between the inner wall of the bore 6 of the femur 4 and the corresponding bone piece 2 by using the same fixation tool 8 so that the bone piece 2 may be similarly secured against the inner wall of the bore 6 of the femur 4.

As a result, the graft bone pieces 2 are firmly secured to the femur 4 and the tibia 5, respectively, and the damaged tendon between the femur 4 and the tibia 5 is allowed to rebuild itself while the graft tendon 1 extending between the two bone pieces 3 keeps the femur 4 and the tibia 5 together.

Figure 2:
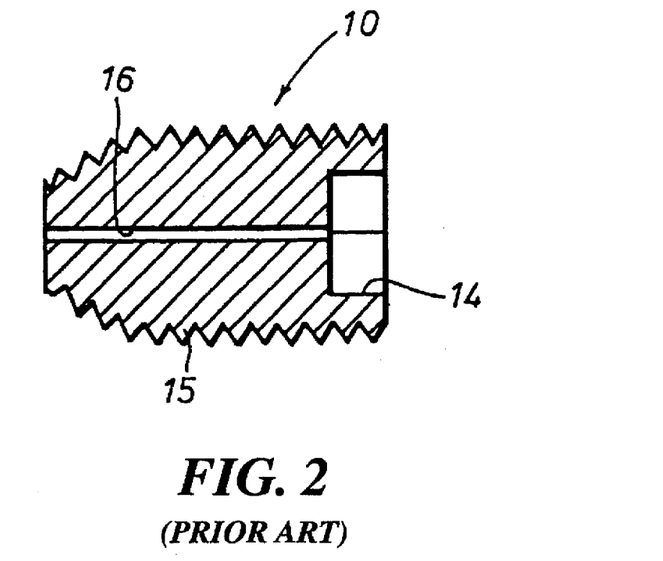
FIG. 2 is a longitudinal sectional view of a conventional screw member used for securing a graft bone piece to a bone part.
Figure 3:
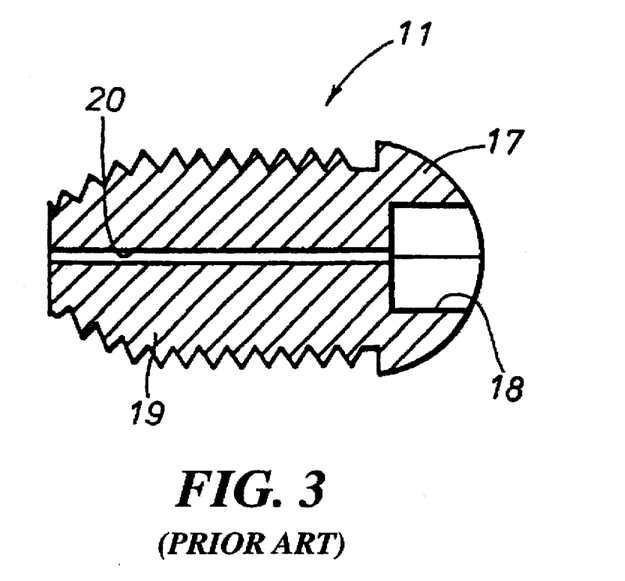
FIG. 3 is a longitudinal sectional view of another conventional screw member.
Figure 4:
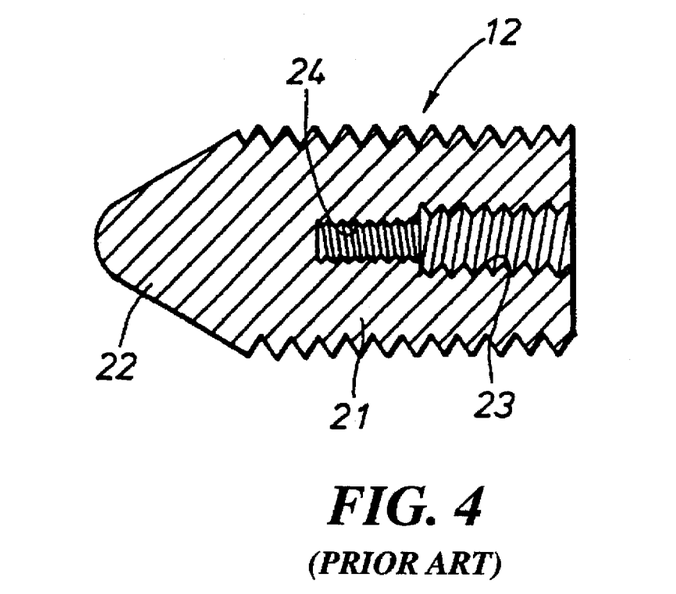
FIG. 4 is a longitudinal sectional view of yet another conventional screw member.
Figure 5:
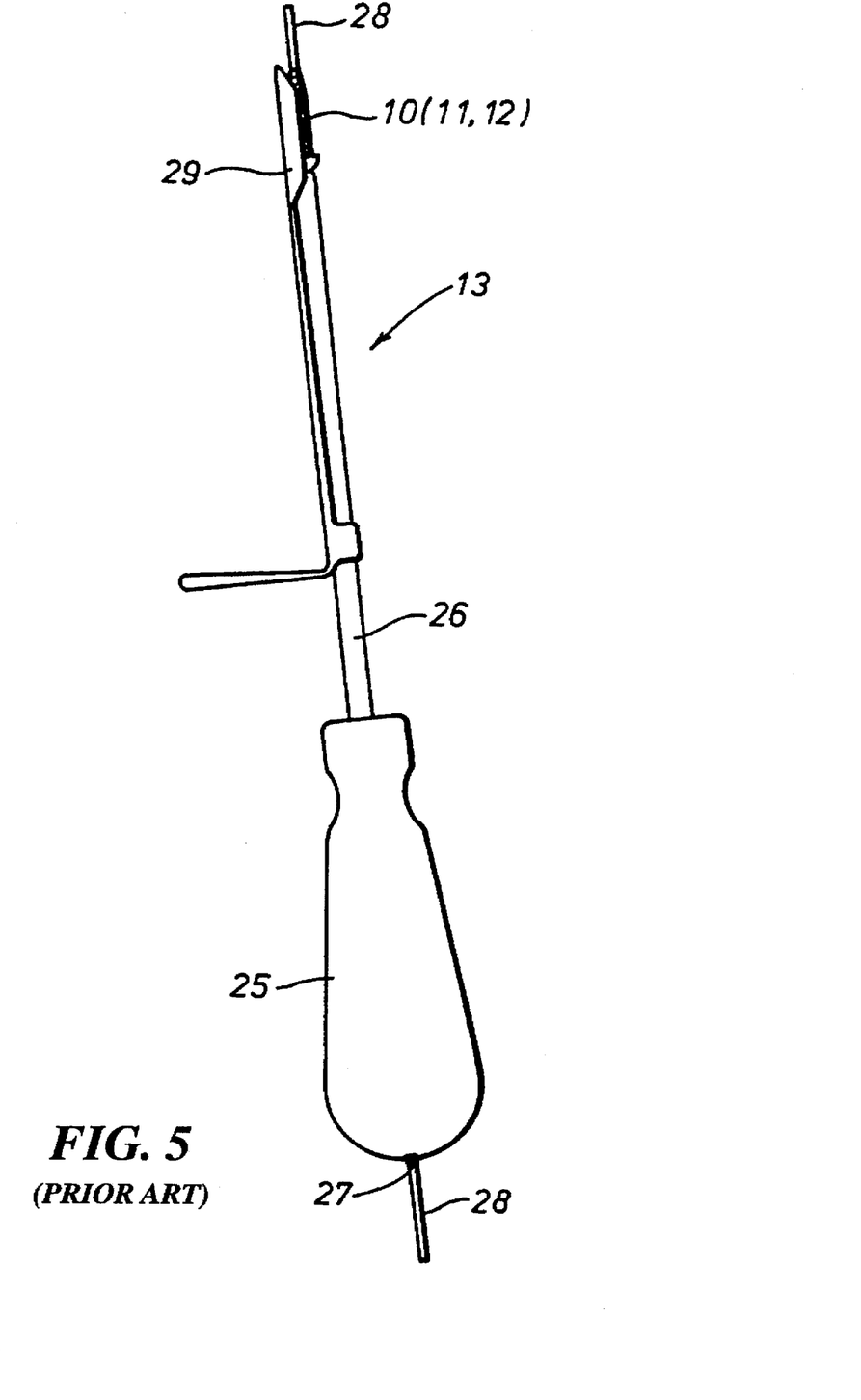
FIG. 5 is an overall front view of a conventional graft bone fixation tool.

In such a tendon reconstruction surgery, screw members 10, 11 and 12 illustrated in FIGS. 2 to 4 in combination with a fixation tool 13 such as the one illustrated in FIG. 5 have conventionally been used.

The screw member 10 illustrated in FIG. 2 consists of a screw shank 15 which is provided with an engagement recess 14, adapted to be engaged by a bit formed at the tip of the fixation tool 13, in a base end surface thereof, and is generally provided with a tapered profile defined by a base section having a straight (parallel) thread and a free end section having a taper thread, and an inner guide bore 20 passed axially entirely through the screw member 10.

The screw member 11 illustrated in FIG. 3 comprises a screw head 17 having an engagement recess 18 adapted to be engaged by a bit formed at the tip of the fixation tool 13, a screw shank 19 having a generally tapered profile defined by a base end section provided with a straight thread, and a free end section provided with a taper thread, and an inner guide bore 20 passed axially entirely through the screw member 11.

The screw member 12 illustrated in FIG. 4 consists of a screw shank 21 having a straight screw thread around its outer circumference, and is provided with a conical guide projection 22 at a tip thereof. The screw member 12 is further provided, in an axial center of the base end thereof, with a larger threaded bore 23 for engaging a bit for fastening the screw member, and a smaller coaxial bore 24 having a reversed thread for engaging a bit for unfastening the screw member 12.

Referring to FIG. 5, the fixation tool 13 comprises a rotary drive unit 25 adapted to be gripped by hand, and a transmission shaft 26 which is integrally attached to the rotary drive unit 25, and is formed with a bit at a free end thereof for engagement with associated engagement means, typically consisting of a hexagonal recess, provided in the screw member 10 (11 or 12). When a screw member having an axial bore such as the screw members 10 and 11 is used, an axial bore 27 is also formed in the rotary drive unit 25 and the transmission shaft 26 so that the guide wire 28 for facilitating the insertion of the screw member may be passed through this axial bore 27 and the bore of the screw member 10. Depending on the kind of the screw member, a protector 29 may be fitted on the transmission shaft 26 so as not to damage the surrounding tissues and the graft tendon.

Such conventional arrangements, which employ a screw member such as those described above in combination with the fixation tool as described above, are known to have a number of problems that need to be resolved.

For instance, because the engagement means (engagement recesses 14 and 18) for engaging the bit of the fixation tool 13 is relatively shallow as is the case with the screw members 10 and 11 illustrated in FIGS. 2 and 3, the necessary torque to firmly thread the screw member into the gap between two adjacent bone parts may not be effectively transmitted to the screw member. Particularly when the length of the straight thread section is increased resulting in the higher securing force, a relatively large effort is therefore required to turn the screw member. It is possible that the bit may be dislodged from the engagement recess of the screw member and thereby damage the adjacent bone parts.

Also, due to possible misalignment of the axial center of the screw member from the intended path of insertion, the so-called screw diversion may occur so that the graff bone pieces 2 may not be secured accurately and firmly enough for the tendon to recover to its original condition in a satisfactory manner following the surgery.

When the engagement means for engaging the bit of the fixation tool 13 consists of larger and smaller threaded bores 23 and 24 which are coaxial with each other as is the case with the screw member 12 of FIG. 4, two separate tools will be needed for inserting and removing the screw member, respectively. In particular, when removing the screw member by using the smaller threaded bore 24, the screw thread may not be able to withstand the large torque that may be required to remove the screw member 12.

When a tapered threaded section or a guide projection is provided in a free end of the screw shank as is the case with the screw members 10 and 11 of FIGS. 2 and 3, if the screw member is forced too deeply into the gap between two bone parts or the remodeling of the bore in the bone has occurred, the pointed tip of the screw member may damage the surrounding tissues and the graff tendon. Even if the screw member is properly threaded into the gap between two bone parts, because the tapered section is not effective in securing the screw member, and the effective length of the screw thread is limited to the straight thread section of the screw member, the securing force for the bone parts may not be sufficient, and the rehabilitation of the patient may be undesirably prolonged.

More specifically, the length of a graff bone piece harvested from a patella of a person is no more than 20 to 25 mm, and the effective length of the screw member is desired to correspond to this length so as to maximize the securing force. However, because of the provision of a tapered section and a guide projection, the effective length of the screw member tends to be insufficient to achieve a sufficient force for engagement. If the effective length of the screw member is increased, the overall length of the screw member becomes so large that the tapered section or the guide projection projects toward the graff tendon, thereby increasing the possibility of damaging the graff tendon.

Thus, the problems of the prior art may be summarized as follows. Because the effective threaded section of a screw member is limited to its straight or parallel thread section, it may be desired to eliminate any tapered section to maximize the securing force for a given length of the screw member. However, this causes a substantial difficulty in inserting the screw member into a gap in the bone due to lack of a guiding action of its free end. This may be overcome to a certain extent by increasing the thickness of the guide wire. The improved guiding action of the guide wire may allow the use of a screw member without any tapered section.

A thick guide wire however still has two problems. First of all, because the bore for passing the guide wire has to be provided in the bit of the fixation tool also, the provision of such a large central bore in the bit may reduce the mechanical strength of the bit to an unacceptable level. It may collapse when it is engaged with a screw head, and a substantial torque is applied to the bit. Secondly, the diameter of the guide wire is therefore necessarily less than the diameter of the bit, and a somewhat blunt annular shoulder is inevitably defined between the free end of the screw member and the guide wire. The blunt annular shoulder is obviously highly detrimental to the smooth insertion of the screw member.

BRIEF SUMMARY OF THE INVENTION

In view of such problems of the prior art, a primary object of the present invention is to provide a graft bone fixation tool which allows a graft bone piece to be securely lodged in a bore formed in a bone part.

A second object of the present invention is to provide a graft bone fixation tool which can be easily used without requiring any undue effort for inserting a screw member into a gap between two bone parts.

A third object of the present invention is to provide a screw member for insertion between two bone parts which provides a sufficient securing force.

A fourth object of the present invention is to provide a screw member for insertion between two bone parts which would not damage the graft tendon and the surrounding tissues.

According to the present invention, such objects can be accomplished by providing a graft bone fixation tool, comprising: a transmission shaft including a typically tapered forward tip and an intermediate section provided with engagement means for torque transmission, the transmission shaft being adapted to be fitted into and through an axial bore of a screw member provided with associated engagement means for cooperation with the engagement means of the transmission shaft, the screw member being provided with a screw thread around an outer circumference thereof; and a rotary drive unit provided at a base end of the transmission shaft for manually rotating the transmission shaft so as to apply a torque to the screw member fitted on the intermediate section of the transmission shaft.

Thus, the screw member may be provided with a strictly straight thread without any section of taper thread because the forward end of the transmission shaft provides the necessary guide action, the entire length of the screw member can be threaded with the graft bone piece, and the securing force of the screw member for a given length thereof can be maximized. Also, because the forward tip of the screw member would not project toward the graft tendon with the result that, as opposed to the conventional screw members provided with a section of taper thread or a guide projection at its tip, the tip of the screw member would not damage the graft tendon or the surrounding tissues while the force effective in securing the graft bone piece is maximized. Because the screw member is turned by the transmission shaft with the inner circumference of the screw member fully engaged with the transmission shaft over the entire length of the screw member, the drive torque is effectively transmitted to the screw member, and the screw member can be firmly threaded into the gap. Also, the dislodgment of the bit from the transmission shaft or the deformation of the engagement means can be avoided, and the transmission shaft provides a favorable guiding action.

The transmission shaft may be provided with an axial bore for passing a guide wire therethrough. In that case, because no taper need to be provided in the tip of the screw member, a guide shaft of a relatively large diameter can be extended from the tip of the screw member with the result that diverging of the movement of the screw member from the intended path of insertion can be avoided as opposed to the conventional guide wire which is known to be too flexible for effective guide action.

The screw member may consist of a hollow cylindrical member having a strictly straight thread around its circumference. And, its axial bore may be either straight bore having a uniform diameter or have a stepped shape defining an annular shoulder facing the rotary drive unit.

According to a preferred embodiment of the present invention, the rotary drive unit comprises a handle grip, a rotary tube integrally attached to the handle grip, and an axial bore passed through the handle grip and the rotary tube for receiving the intermediate section of the transmission shaft in an axially slidable but rotatively integral manner, a free end of the rotary tube being adapted to abut an opposing axial end of the screw member.

According to a second preferred embodiment of the present invention, the rotary drive unit comprises a handle grip, and a base end of the transmission shaft is integrally attached to the handle grip, the fixation tool further comprising an adjustment tube that can be fitted on the transmission shaft in such a manner that a free end of the rotary tube abuts an opposing axial end of the screw member when the screw member is fitted on the intermediate section of the transmission shaft in an axially slidable but rotatively integral manner.

According to a third preferred embodiment of the present invention, the rotary drive unit comprises a handle grip, and a base end of the transmission shaft is integrally attached to the handle grip, the transmission shaft comprising a base end section, extending between the intermediate section and the handle grip, which has a larger outer diameter than the intermediate section so as to define an annular shoulder facing away from the handle grip.

BRIEF DESCRIPTION OF THE DRAWINGS

Now the present invention is described in the following with reference to the appended drawings, in which:

FIG. 12 is a cross-sectional view of a blocker of the invention.

DETAILED DESCRIPTION OF THE PREFERRED EMBODIMENTS

Figure 6A:
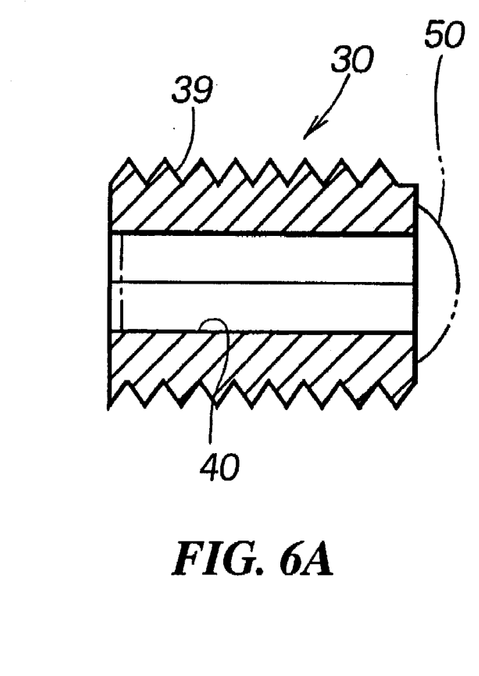
FIGS. 6a to 6c are schematic views showing an embodiment of the screw member and an associated transmission shaft used in the graft bone fixation tool of the present invention.
Figure 6B:
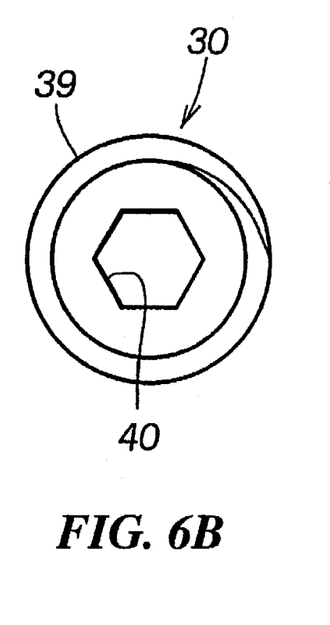

FIGS. 6a and 6b illustrate an embodiment of the screw member 30 according to the present invention which essentially consists of hollow cylindrical member having a straight (parallel) screw thread 39 on outer circumferential surface thereof, and a bore 40 having a hexagonal cross section and passed axially entirely through the screw member 30. The material of the screw thread typically consists of an alloy having a property suitable for use in living tissues, but may also consist of suitable plastic material.

Figure 6C:
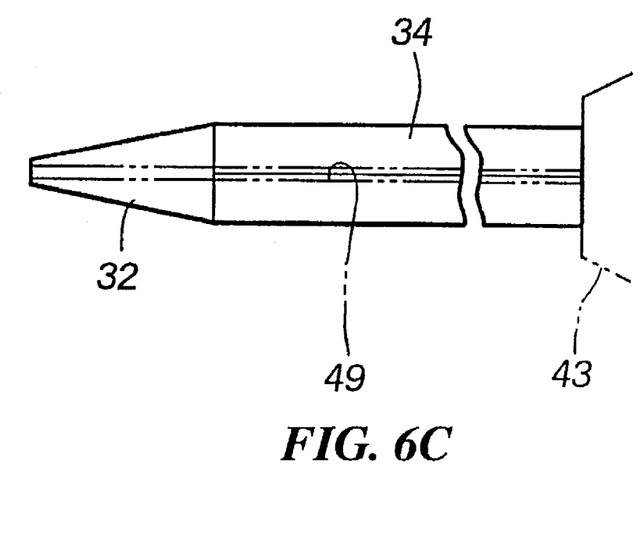
Figure 7:
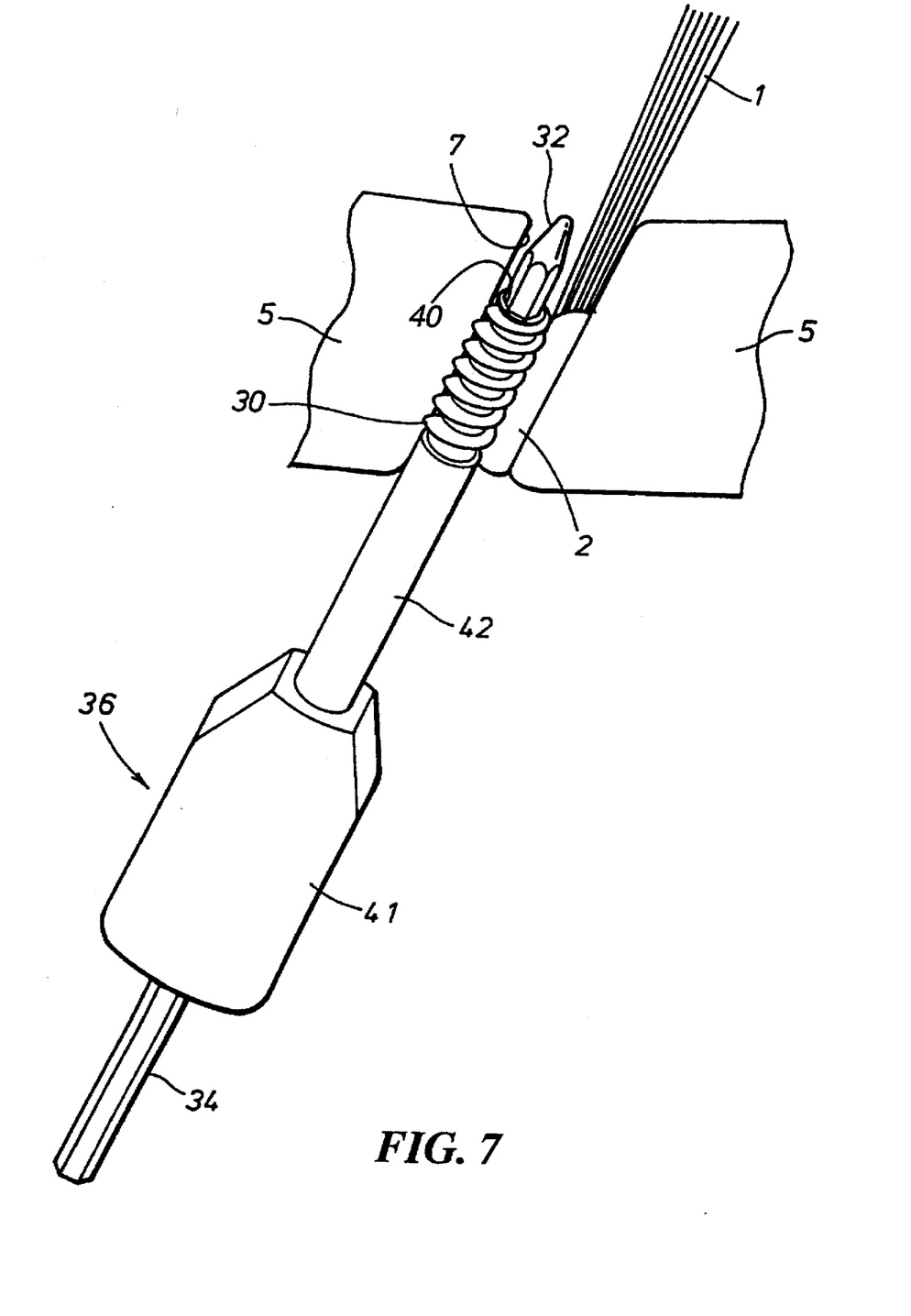
FIG. 7 is an perspective view showing a first embodiment of the graft bone fixation tool according to the present invention, along with the manner in which this tool is used for inserting a screw member into a gap between a graft bone piece and an adjacent wall of a bore formed in a bone part.
Figure 8:
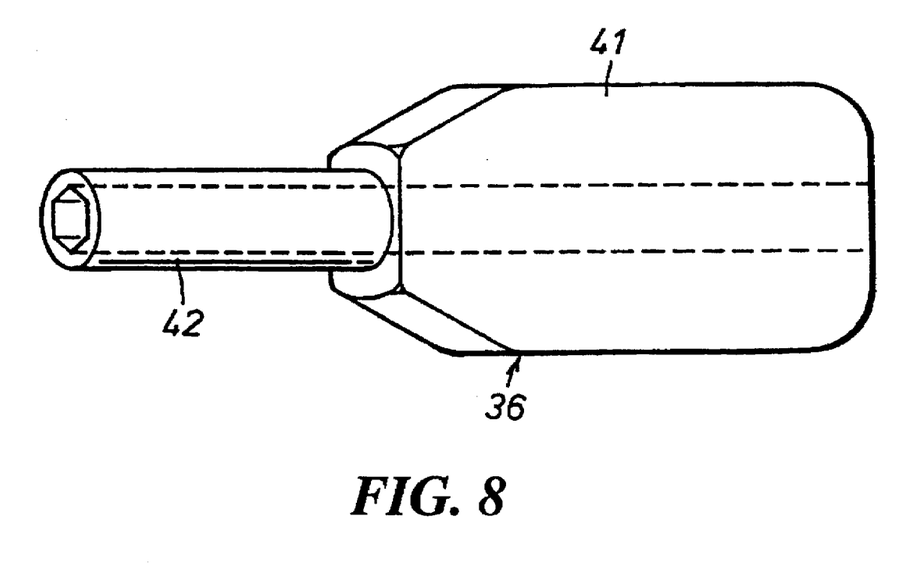
FIG. 8 is a perspective view showing the handle grip of the graft bone piece fixation tool illustrated in FIG. 7.

Referring to FIG. 7, the graft bone fixation tool according to the present invention comprises a transmission shaft 34 which is adapted to be snugly passed through the bore 40 of the screw member 30 in an axially slidable but rotatively integral manner, and a rotary drive unit 36 which is provided with an axial bore for snugly receiving the transmission shaft 34 likewise in an axially slidable but rotatively integral manner. As illustrated in FIG. 8, the rotary drive unit 36 comprises a handle grip 41 adapted to be held by hand, and a rotary tube 42 integrally attached to the handle grip 41. The axial bore of the rotary drive unit 36 passes through the handle grip 41 and the rotary tube 42. As shown in FIG. 6c, the free end of the transmission shaft 34 is provided with a tapered, rounded or otherwise pointed tip 32. As discussed hereinafter, the transmission shaft 34 may be optionally provided with an axial bore 49 which extends over its entire length so that a guide wire may be passed therethrough.

How this fixation tool is used for threading the screw member 30 into a gap between the graft bone piece 2 and the wall of the bore 7 formed in the tibia 5 is now described in the following with reference to FIG. 7.

First of all, the transmission shaft 34 is passed through the axial bore of the rotary drive unit 36, and the screw member 30 is fitted on the forward end of the transmission shaft 34 projecting from the free end of the rotary shaft 42. The forward end of the transmission shaft 34 is then passed into the gap defined between the graft bone piece 2 and the adjacent wall of the bore 7 formed in the tibia 5. The tapered forward end of the transmission shaft 34 provides a guiding action for the insertion of the screw member 30 in the gap between the two bone parts. Once the screw member 30 is placed at the mouth of the gap, the screw member 30 can be urged into the gap by holding the handle grip 41 by hand, and pushing the rear end of the screw member 30 with the forward end of the rotary tube 42. By turning the handle grip 41 by hand in this condition, the screw member 30 may be threaded into the gap. The necessary torque can be positively transmitted from the grip handle 41 to the screw member 30 via the transmission shaft 34 by virtue of the complementary shape of the inner bore 40 of the screw member 30, and the inner bore of the rotary drive unit 36. Because the transmission shaft 34 is passed axially through the screw member 30, the diversion of the screw member 30 from the intended path for insertion can be positively prevented, and the screw member 30 can be accurately guided into the gap.

Once the screw member 30 is threaded into the gap by a prescribed distance, the transmission shaft 34 and the rotary drive unit 36 can be removed from the screw member 30 by pulling them away from the screw member 32.

Figure 9:
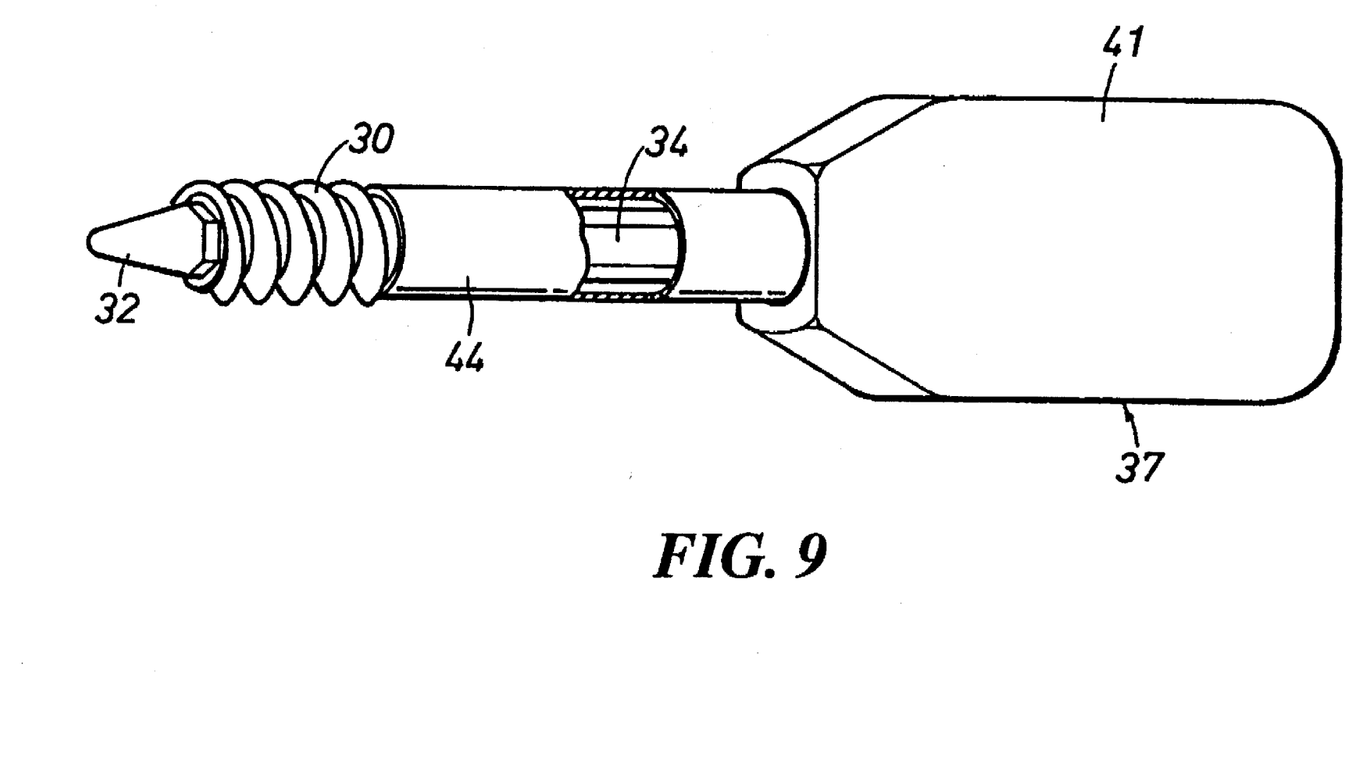
FIG. 9 is a partly broken away perspective view of a second embodiment of the graft bone fixation tool according to the present invention.

The fixation tool illustrated in FIG. 9, is similar to the embodiment shown in FIG. 7 where the base end of the transmission shaft 34 is integrally attached to the handle grip 41, and to provides a support for the screw member 30 from the rear as the rotary tube 42. An adjustment tube 44, which may be selected from a plurality of adjustment tubes having different lengths, is interchangeably fitted on the transmission shaft 34. The operation and the function of this fixation tool are otherwise similar to those of the first fixation tool.

Figure 10:
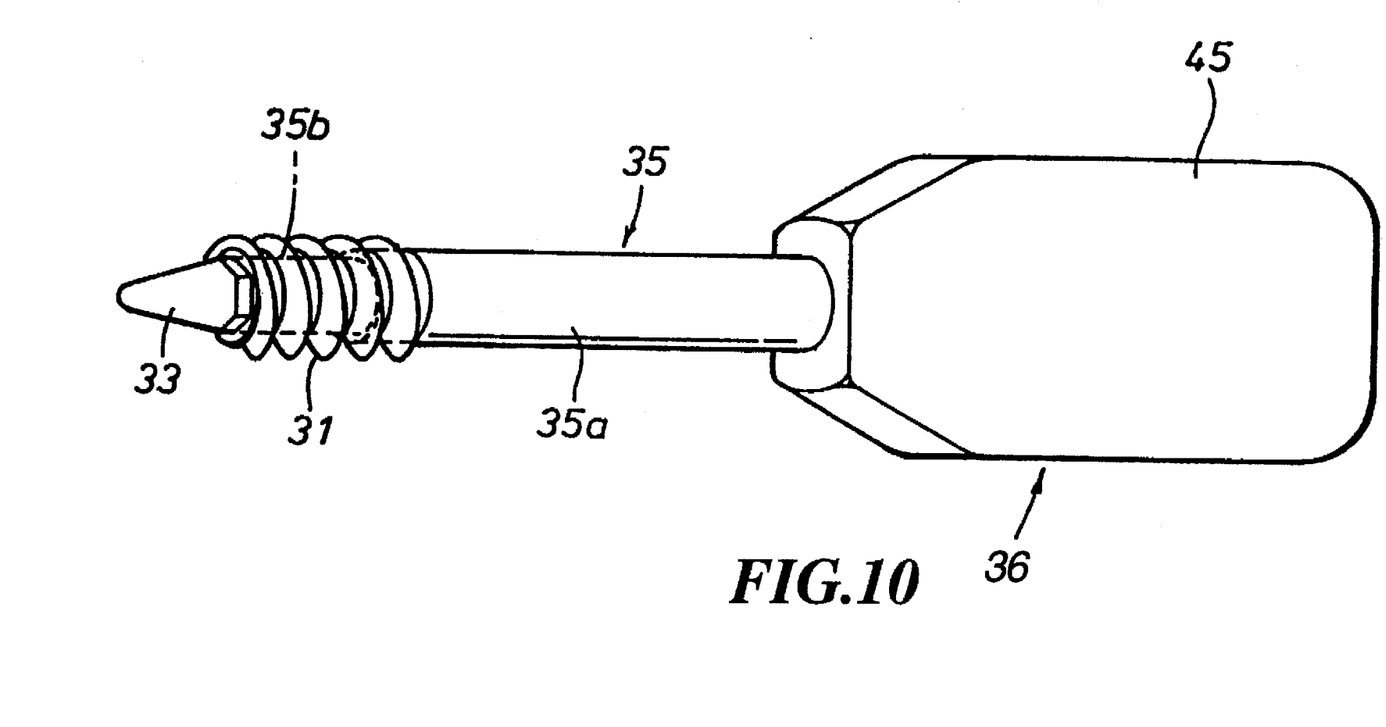
FIG. 10 is a perspective view of a third embodiment of the graft bone fixation tool according to the present invention.
Figure 11A:
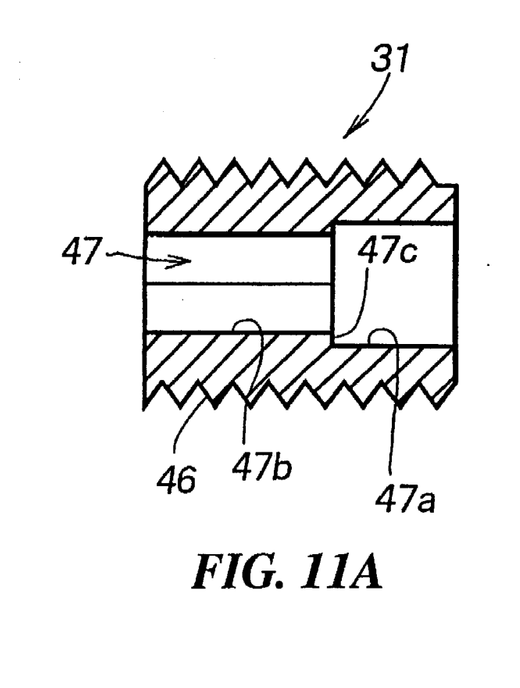
FIGS. 11a, 11b and 11c are views similar to FIGS. 6a, 6b and 6c, respectively, showing an alternate embodiment of the screw member suitable for use with the third embodiment illustrated in FIG. 10, along with the associated transmission shaft of the graff bone fixation tool illustrated in FIG. 10.
Figure 11B:
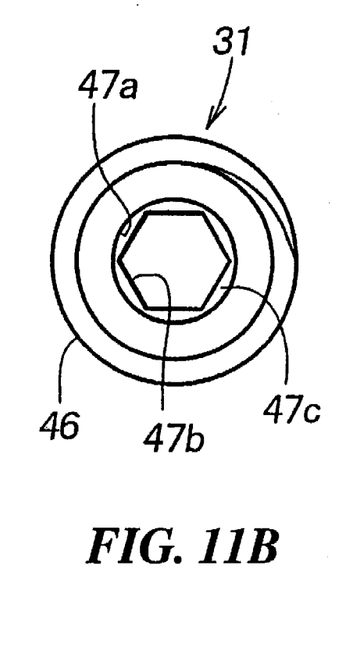
Figure 11C:
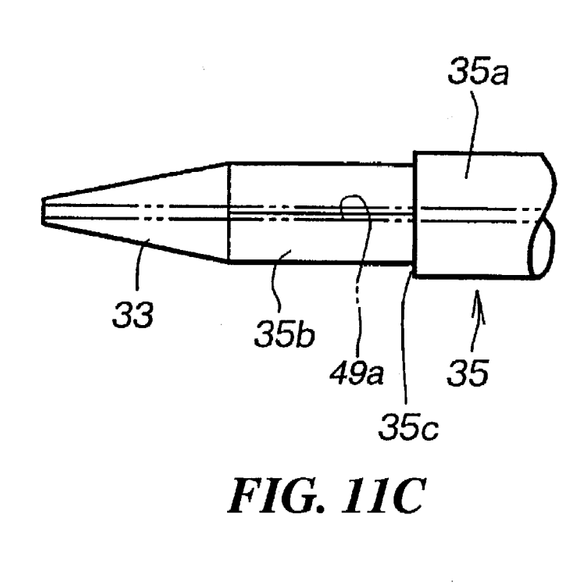

In the case of the third embodiment of the graft bone fixation tool illustrated in FIG. 10, the transmission shaft 35 is likewise integrally attached to the handle grip 45 of the rotary drive unit 36. The base end section 35a of the transmission shaft 35, which is provided with a round cross section as illustrated in FIG. 11, is integrally attached to the handle grip 45, and the free end of the transmission shaft is provided with an intermediate section 35b having a hexagonal cross section, and a tapered tip 33 which provides a guiding action similarly as the tapered tips of the first and second embodiments. Because the outer diameter of the base end section 35a is at least larger than the minimum outer diameter of the intermediate section 35b, an annular shoulder 35c is defined between the hexagonal intermediate section 35b and the round base end section 35a. In this case, as illustrated in FIGS. 11a and 11b, the screw member 31 likewise consists of a hollow cylindrical member having a straight thread 46 around its outer circumference. The screw member 31 is provided with an axial bore 47 consisting of a base end section 47a having a circular cross section corresponding to that of the base end section 35a of the transmission shaft 35, and a free end section 47b having a hexagonal cross section corresponding to that of the intermediate section 35b of the transmission shaft 35. An annular shoulder 47c is defined between the base end section 47a and the free end section 47b of the axial bore 47 of the screw member 31.

According to the third embodiment of the fixation tool, once the screw member 31 is fitted on the transmission shaft 35, the screw member 31 is rotatively engaged by the intermediate section 35b of the transmission shaft, and the screw member 31 is supported from the rear by the annular shoulder 35c of the transmission shaft 35 engaging the associated annular shoulder 47c defined in the axial bore 47 of the screw member 31. The operation and the function of this fixation tool are similar to those of the second embodiment of the graft bone fixation tool.

Sometimes, the screw member may consist of a material which can be gradually absorbed by the living body. Therefore, the screw member is not required to be removed after the bone has been fully reconstructed. In such a case, the wall thickness of the screw member may prematurely diminish by being absorbed by the living body during use, and may lose the required mechanical strength over time. Therefore, if the original wall thickness is too small or the material of the screw member is absorbed by the living body too rapidly, the screw member may prematurely collapse under the pressure from the surrounding bone which has grown over time. Therefore, depending on various conditions, it may be desirable to place a plug called a "blocker" into the central bore of the screw member after the screw member has been securely lodged in the bone part. By doing so, the screw member can retain its mechanical strength against external pressure. The blocker may also consist of a material which can be absorbed by the living body. As one can readily appreciate, the use of such a blocker is not limited to the case where a material that can be absorbed by the living body is used. When the material of the screw member is not provided with a sufficient mechanical strength by itself against the external pressure applied thereto by the surrounding bone part growing over time, it is advantageous to use a blocker.

Figure 12:
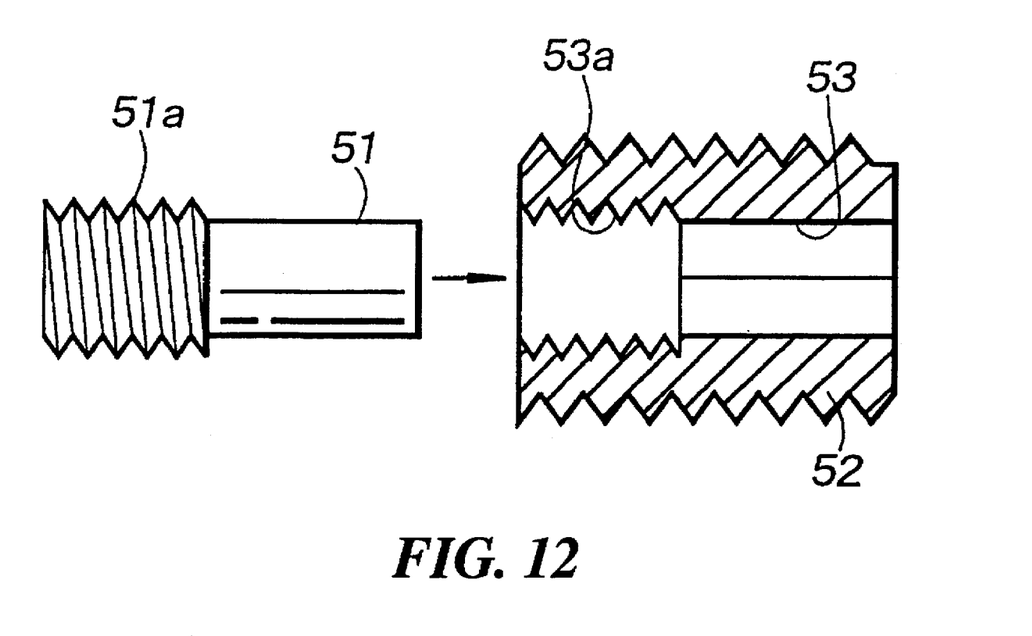
FIG. 12 illustrates another embodiment of the screw member fitted with a blocker according to the principles of this invention.

In FIG. 6a is illustrated, in imaginary lines, a blocker 50 which is fitted into the central bore 40 of the screw member 30. FIG. 12 illustrates yet another embodiment of the screw member 52 fitted with a blocker 51. In this case, the blocker 51 as well as the associated central bore 53 is provided with a threaded section 51a and 53a for securely retaining the blocker 51 in the central bore 53 of the screw member 51.

The present invention is not limited by the above described embodiments, and can be variously modified without departing from the scope of the present invention.

For instance, the screw member was provided strictly with a straight thread around its outer circumference over its entire length in the above described embodiments, but may be partly provided with a taper thread and/or a guide projection to an extent permissible in each application without departing from the spirit of the present invention. Obviously, the screw member is typically provided with some chamfering, and it should not be considered as deviating from the teaching of this patent application.

The engagement means used between the screw member and the transmission shaft as well as that optionally used between the transmission shaft and the rotary drive unit is not limited to the arrangement involving a hexagonal cross section, but may consist of any arrangement as long as it allows the two parts to be separated away from each other in the axial direction but firmly secures the two parts together for integral rotation with each other.

In the same way as the bore was formed in the axial center of the conventional fixation tool for passing the guide wire therethrough, bore 49 (FIG. 6c) and bore 49a (FIG. 11c) may be passed through the transmission shaft and the rotary drive unit so as to receive the guide wire, and thereby guide the transmission shaft to the intended path of insertion in a similar fashion to the conventional practice.

The advantages of the present invention may be summarized as given in the following, but it should not be understood as being exclusive of other possible advantages.

Because the screw member is turned by the transmission shaft with the inner circumference of the screw member fully engaged with the transmission shaft over the entire length of the screw member, the drive torque is effectively transmitted to the screw member, and the screw member can be firmly threaded into the gap. Also, the dislodgment of the bit from the transmission shaft or the deformation of the engagement means can be avoided.

The screw member is not thrown off from the axial center as it is threaded into the gap because it is securely supported by the transmission shaft which is passed through the screw member. Therefore, the graff bone piece can be easily and reliably attached to a desired location without damaging the graff tendon or the surrounding tissues.

When the screw member is provided with a strictly straight thread without any section of taper thread, the entire length of the screw member can be threaded with the graff bone piece 2, and the securing force of the screw member for a given length thereof can be maximized. Also, because the forward tip of the screw member would not project toward the graff tendon with the result that, as opposed to the conventional screw members provided with a section of taper thread or a guide projection at its tip, the tip of the screw member would not damage the graff tendon or the surrounding tissues while the force effective in securing the graff bone piece is maximized.

Furthermore, when there is no taper in the tip of the screw member, because a guide shaft of a relatively large diameter can be extended from the tip of the screw member, diverging of the movement of the screw member from the intended path of insertion can be avoided as opposed to the conventional guide wire which is known to be too flexible for effective guide action.

Although the present invention has been described in terms of preferred embodiments thereof, it is obvious to a person skilled in the art that various alterations and modifications are possible without departing from the scope of the present invention which is set forth in the appended claims.

What we claim is:

1. A graft bone fixation tool for securing a bone piece, which is attached to one end of a length of tendon, in a bore formed in a bone part, comprising:

a transmission shaft including a forward tip and an intermediate section provided with engagement means for torque transmission, said transmission shaft being adapted to be slidingly fitted into and through an axial bore of a screw member, said transmission shaft being of a length such that said forward tip extends from the screw member axial bore, the screw member being provided with associated engagement means for cooperation with said engagement means of said transmission shaft, the screw member being provided with a screw thread around an outer circumference thereof for insertion into a gap between the bone piece and the bore;

a rotary drive unit provided at a base end of said transmission shaft for manually rotating said transmission shaft so as to apply a torque to the screw member fitted on said intermediate section of said transmission shaft;

wherein said forward tip of said transmission shaft is provided with a tapered or otherwise pointed tip which guides the screw member in a desired direction into the gap; and wherein said rotary drive unit comprises a handle grip, a rotary tube integrally attached to said handle grip, and an axial bore passing through said handle grip and said rotary tube for receiving said intermediate section of said transmission shaft in an axially slidable but rotatively engaged manner, a free end of said rotary tube being adapted to support an opposing axial end of the screw member.

2. A graff bone fixation tool according to claim 1, wherein said screw member consists of a hollow cylindrical member having a strictly straight thread around its circumference.

3. A graft bone fixation tool comprising:

a transmission shaft including a forward tip and an intermediate section provided with engagement means for torque transmission, said transmission shaft being adapted to be slidingly fitted into and through an axial bore of a screw member, said transmission shaft being of a length such that said forward tip extends from the screw member axial bore, the screw member being provided with associated engagement means for cooperation with said engagement means of said transmission shaft, the screw member being provided with a screw thread around an outer circumference thereof for insertion into a gap between the bone piece and the bore;

a rotary drive unit provided at a base end of said transmission shaft for manually rotating said transmission shaft so as to apply a torque to the screw member fitted on said intermediate section of said transmission shaft;

wherein said forward tip of said transmission shaft is provided with a tapered or otherwise pointed tip which guides the screw member in a desired direction into the gap; and wherein said rotary drive unit comprises a handle grip, and a base end of said transmission shaft is integrally attached to said handle grip, said fixation tool further comprising an adjustment tube having a first end and a second end fittable on said transmission shaft in such a manner that said first end of said adjustment tube abuts said handle grip, said second end of said adjustment tube supports an opposing axial end of the screw member when the screw member is fitted on said intermediate section of said transmission shaft in an axially slidable but rotatively engaged manner.

4. A graft bone fixation tool according to claim 1, wherein said inner bore of the screw member is provided a base end section which is complementary in cross section to said base end section of said transmission shaft, and a free end section which is complementary in cross section to said intermediate section of said transmission shaft so that an annular shoulder facing said handle grip is defined between said base end section and said free end section of said axial bore of the screw member for cooperation with an annular shoulder on said transmission shaft.

5. A graft bone fixation tool according to claim 1, wherein said transmission shaft is provided with an axial bore for passing a guide wire therethrough.

\* \* \* \* \*